Figure 1:
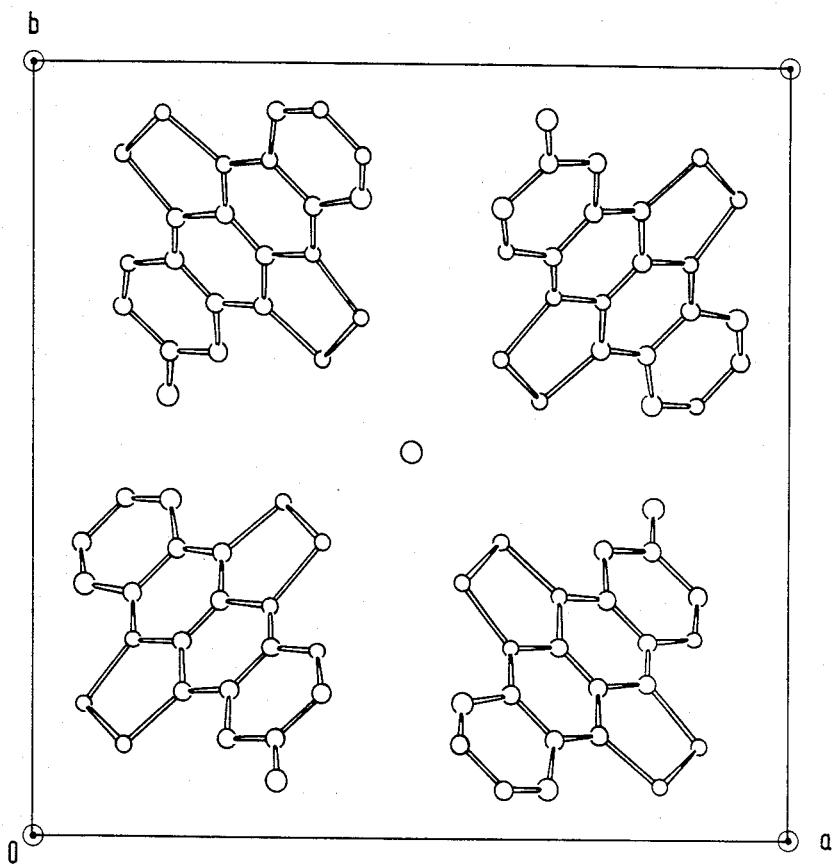

United States Patent [19]

Hilti et al.

[11] Patent Number: 4,522,754
[45] Date of Patent: Jun. 11, 1985

[54] METALLICALLY CONDUCTING (2-FLUORO-5,6,11,12-TETRASELENOTETRACENE)₂-BROMIDE

[75] Inventors: Bruno Hilti, Basel; Carl W. Mayer, Riehen; Grety Rihs, Muttenz, all of Switzerland

[73] Assignee: Ciba Geigy Corporation, Ardsley, N.Y.

[21] Appl. No.: 548,048

[22] Filed: Nov. 2, 1983

[30] Foreign Application Priority Data

Dec. 11, 1982 [CH] Switzerland ............ 6611/82

[51] Int. Cl.³ .............. C07D 517/06; H01B 1/00; B32B 9/04
[52] U.S. Cl. .............. 260/239 R; 204/158 HA; 260/694; 252/500; 361/433; 562/460; 568/326; 570/183; 428/411
[58] Field of Search ................. 260/239 R

[56] References Cited

U.S. PATENT DOCUMENTS 4,384,025  5/1983  Hilti et al. ................. 428/411

OTHER PUBLICATIONS

Hilti et al., Chem. Abst., vol. 101, 202610p, (1984).
Hilti et al., Chem. Abst., vol. 86:181613w, (1977).
Schwartz, Chem. Abst., vol. 88, 152468p, (1978).
Institute of Chemical Physics, USSR Academy of Sciences—I. F. Shchegolev and E. B. Yagubskii, Cation-Radical Salts of Tetraselenotetracene: Synthetic Aspects and Physical Properties, pp. 385–434, 1982.
Chemica Scripta, 1981, 17, 23–26, B. M. Gorelov—Influence of the Nonstoichiometry and Pressure on the Metal–Insulator Transition in the Organic Metal TTT 1.
Helvetica Chimica Acta, vol. 61, Fasc. 4, pp. 1462–1469, (1978), Electrical Properties and Structure of the Organic Metallic . . .
Beilsteins Handbuch der Organischen Chemie, pp. 2547–2549, Viertes Erganzungswerk—Springer–Verlag, Berlin, 1980.
Chemical Abstracts, vol. 54, May 10–Jun. 25, 1960.

Primary Examiner—Donald G. Daus
Assistant Examiner—Cecilia Shen
Attorney, Agent, or Firm—Michael W. Glynn

[57] ABSTRACT

The novel complex of the formula I

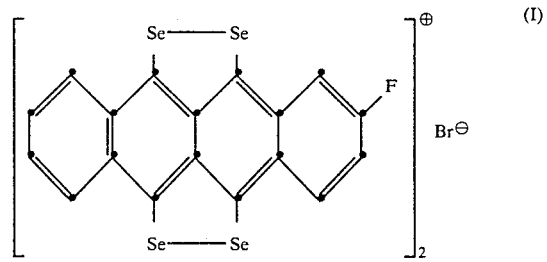

can be produced for example by electrochemical oxidation of 2-fluoro-5,6,11,12-tetraselenotetracene in the presence of an inert organic solvent and a bromide-containing electrolyte. The novel 2-fluoro-5,6,11,12-tetraselenotetracene can for its part be produced by reacting 2,3-naphthalenedicarboxylic anhydride, in the presence of a Friedel-Crafts catalyst, with fluorobenzene to 2-(4-fluorobenzoyl)-naphthalene-3-carboxylic acid; cyclizing this to 2-fluoro-5,12-naphthacenequinone; reducing the 2-fluoro-5,12-naphthacenequinone to 2-fluorotetracene; reacting the 2-fluorotetracene with sulfuryl chloride to 2-fluoro-5,11- or 2-fluoro-6,12-dichlorotetracene; and finally reacting the last-mentioned at elevated temperature with selenium to obtain 2-fluoro-5,6,11,12-tetraselenotetracene. The complex of the formula I is metallically conducting, and is distinguished by a stable metallic phase down to at least 5° K. It can be used for example as an organic conductor element.

2 Claims, 2 Drawing Figures

METALLICALLY CONDUCTING (2-FLUORO-5,6,11,12-TETRASELENOTETRACENE)₂-BROMIDE

The invention relates to (2-fluoro-5,6,11,12-tetraselenotetracene)$_2$-bromide as a novel metallically conducting compound, to processes for producing it, and to its use.

There are known from the literature various metallically conducting, chalcogenated tetracene complexes, such as (5,6,11,12-tetraselenotetracene)$_2$-iodide, -bromide or -chloride, or the (5,6,11,12-tetrathiotetracene)$_2$-(iodo)$_3$ complex. These complexes exhibit at temperatures of between about 30° and 45° K. a relatively sharp transition from the metallic to the nonconducting state, that is to say, the metallic phase of these complexes is not stable down to sufficiently low temperatures at which, for example, superconduction can be expected. It is also known that the transition point from the metallic to the nonconducting state in the case of the (tetrathiotetracene)$_2$-(iodo)$_3$ complex can be lowered under pressure or by variation of the stoichiometry (raising of the iodine concentration beyond the ratio 2:3). It is assumed that the stabilisation of the metallic phase in the case of complexes deviating from the exact 2:3 stoichiometric ratio is brought about by an alteration of the band filling. The mechanism which effects under the influence of pressure in the above complexes the stabilisation of the metallic phase is still largely unknown [cp. for example Chemica Scripta, 17, 23 (1981), German Patent Specification No. 2,641,742, Helv. Chim. Acta, 61, 1462 (1978) and Extended Linear Chain Compounds, Publishers J. S. Miller, Plenum Press, New York, 385 (1982)].

It is the object of the present invention to provide a novel compound from the class of chalcogenated, polycyclic aromatic compounds, the metallic phase of which compound is stable down to very low temperatures, in order to thus advance with the metallic phase into the temperature field of possible superconduction.

It has now been found that the complex of the formula I

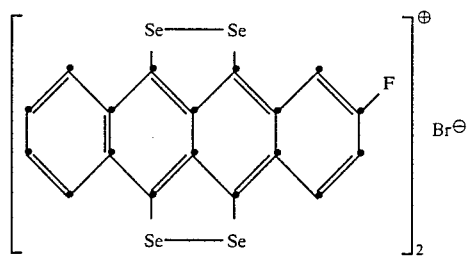

is distinguished by surprisingly having, under normal pressure, and in contrast to for example the aforementioned (tetraselenotetracene)$_2$-iodine, -bromine and -chlorine complexes, a stable metallic phase down to at least 5° K., that is to say, the electrical conductivity of the complex increases continuously from room temperature (20°–25° C.) down to at least 5° K. (= −268° C.). The complex of the formula I has at room temperature an electrical conductivity [$\sigma$] of up to 2000 ohm$^{-1}$ cm$^{-1}$ and at 5° K. one of 6000 ohm$^{-1}$ cm$^{-1}$ (measured along the preferred direction of growth=needle axis).

The complex according to the invention has the space group $P2_12_12_1$. The lengths of the axes of the elementary cell are: a=17.655 Å, b=17.661 Å, c=5.125 Å. The complex is orthorhombic and non-centrosymmetrical and exhibits, besides the high electrical conductivity, a strongly marked electrical and optical anistropy.

The complex according to the invention can be for example in the form of microcrystalline powders, or it can exist as an amorphous layer, as a layer of microcrystals or as amorphous powder, or it can be in the form of single crystals.

Figure 2:
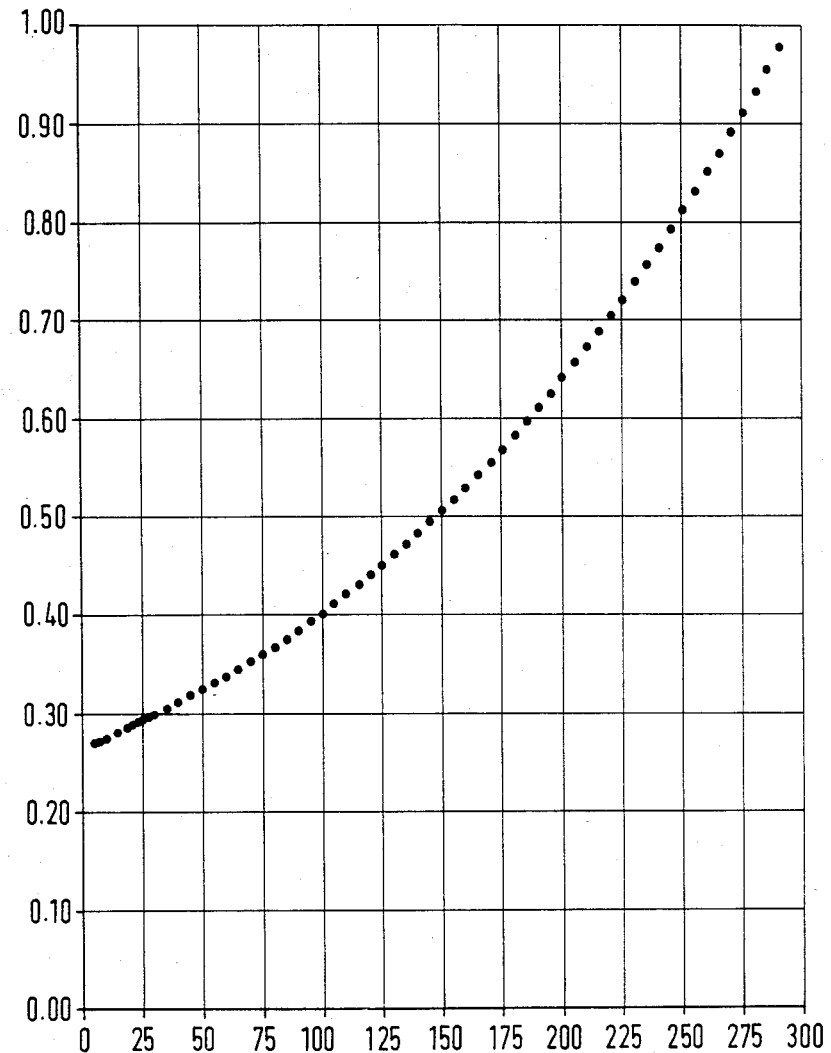

FIG. 1 shows a projection of the crystal structure of the complex according to the invention; and FIG. 2 illustrates the dependence of the electrical resistance of the complex according to the invention on temperature.

The complex of the formula I can be produced by various methods, for example by (direct) oxidation of 2-fluoro-5,6,11,12-tetraselenotetracene with bromine or with an oxidising bromide salt releasing bromine, such as copper(II) bromide and FeBr$_3$, in the presence of an inert organic solvent. Suitable inert organic solvents are for example: halogenated aliphatic hydrocarbons, such as methylene chloride and 1,1,2-trichloroethane; polar substituted, particularly halogenated, aromatic hydrocarbons, such as chlorobenzene, o-dichlorobenzene, 1,2,3-trichlorobenzene, 1,2,4-trichlorobenzene and chlorinated naphthalenes; other polar solvents, such as benzonitrile and alkyl nitriles having 2–5 C atoms, for example acetonitrile, propionitrile and butyronitrile; nitrobenzene; N,N-dialkylamides of aliphatic monocarboxylic acids having 1–4 C atoms in the acid part, for example N,N-dimethylformamide and N,N-dimethylacetamide; N,N,N',N'-tetramethylurea; dialkylsulfoxides, such as dimethyl sufoxide and diethyl sulfoxide; or cyclic ethers, such as tetrahydropyrane, tetrahydrofuran and dioxane. It is also possible to use mixtures of the stated solvents. The reaction temperature for these oxidation reactions is generally between 20° and 120° C.

The complex of the formula I can be produced also by diffusion of bromine from the gas phase, or from a carrier solution, into a solution of 2-fluoro-5,6,11,12-tetraselenotetracene, suitable solvents being those of the type mentioned above.

The complex of the formula I can also be produced from the gas phase, that is, by co-sublimation of 2-fluoro-5,6,11,12-tetraselenotetracene and bromine, using a process analogous to that described in the German Patent Specification No. 2,641,742. In this case, the 2-fluoro-5,6,11,12-tetraselenotetracene and the bromine are advantageously reacted together in an inert gas atmosphere, preferably in an open system. The reaction in the gas phase can be carried out however also in a closed system in an inert gas atmosphere. The reaction in the gas phase can be carried out for example by bringing bromine vapour, by means of an inert carrier gas, into contact with 2-fluoro-5,6,11,12-tetraselenotetracene in the gas phase at about 260° C. The crystals then grow on the walls of the reaction vessel and/or on a substrate optionally arranged in the reaction vessel, such as aluminium oxide or preferably quartz, in any desired form, for example in the form of rods or tubes. The carrier gas used for this method of production is advantageously a high-purity inert gas, such as argon, nitrogen, helium or xenon. The reaction temperatures in the gas-phase reaction are advantageously between 180° and 300° C. The crystals obtained by co-sublimation can be readily removed from the reaction chamber or from the substrate. A suitable experimental arrangement for this production method is described in the German Patent Specification No. 2,641,742 mentioned in the foregoing.

The complex according to the invention is preferably produced however by electrochemical oxidation of 2-fluoro-5,6,11,12-tetraselenotetracene in the presence of an inert organic solvent and a bromide-containing electrolyte. The inert organic solvents used can be those of the type given above. Preferably used are cyclic ethers and N,N-dialkylamides of aliphatic monocarboxylic acids or mixtures thereof, especially tetrahydrofuran and N,N-dimethylformamide or mixtures thereof. Suitable bromide-containing electrolytes are for example salts of the formula II

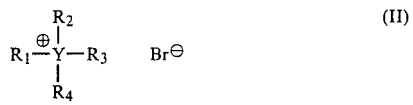

wherein Y is N, P or As, and $R_1$ to $R_4$ independently of one another are each $C_1$-$C_{18}$-alkyl, benzyl, phenyl or naphthyl. Alkyl groups $R_1$ to $R_4$ can be straight-chain or branched-chain and preferably have 1–12 C atoms. Examples of such alkyl groups are: methyl, ethyl, n-propyl, isopropyl, n-butyl, sec-butyl, tert-butyl, 1,1,3,3-tetramethylbutyl, n-pentyl, 2-pentyl, n-hexyl, n-heptyl, n-octyl, n-decyl, n-dodecyl, n-tetradecyl, n-hexadecyl and n-octadecyl. There are preferably used compounds of the formula II wherein Y is N or P, $R_1$ is benzyl or phenyl, and $R_2$ to $R_4$ are straight-chain alkyl each having 1–12 C atoms or phenyl, or $R_1$ to $R_4$ are each straight-chain alkyl having 1–12 C atoms. Compounds of the formula II particularly preferably used are those wherein Y is N, and $R_1$ to $R_4$ are each straight-chain alkyl having 1–6 C atoms, especially n-butyl.

Depending on the temperature of the electrolytic cell and employed solvent, there are advantageously used between 0.01 and 100 g of electrolyte per liter. Devices known per se can be used as electrolytic cells, for example those wherein the anode compartment is separated from the cathode compartment by teflon filters, glass frit or capillaries. The dimensions of the electrolytic cells can vary according to the employed amount of reaction components, but they have virtually no effect on the quality of the complex of the formula I obtained. Cell volumes of 15–100 ml for example are particularly suitable for producing about 5–50 mg of the complex of the formula I.

The reaction temperatures (temperatures of the electrolytic cells) are advantageously between 0° and 120° C. depending on the type of solvent used. The current strength varies in general between 0.005 μA and 5 μA. The diameter of the anodes and cathodes is preferably between 0.1 and 5 mm.

In the above reactions, the 2-fluoro-5,6,11,12-tetraselenotetracene and the bromine or bromide salt are used in at least a stoichiometric amount. In general, however, it is advisable to commence with an excess of bromine or bromide salt, so that in the reaction phase there is at any time a 20- to 1000-fold molar excess of bromine or bromide salt.

The novel intermediates of the formulae III to VI developed for producing the complex of the formula I likewise form subject matter of the present invention.

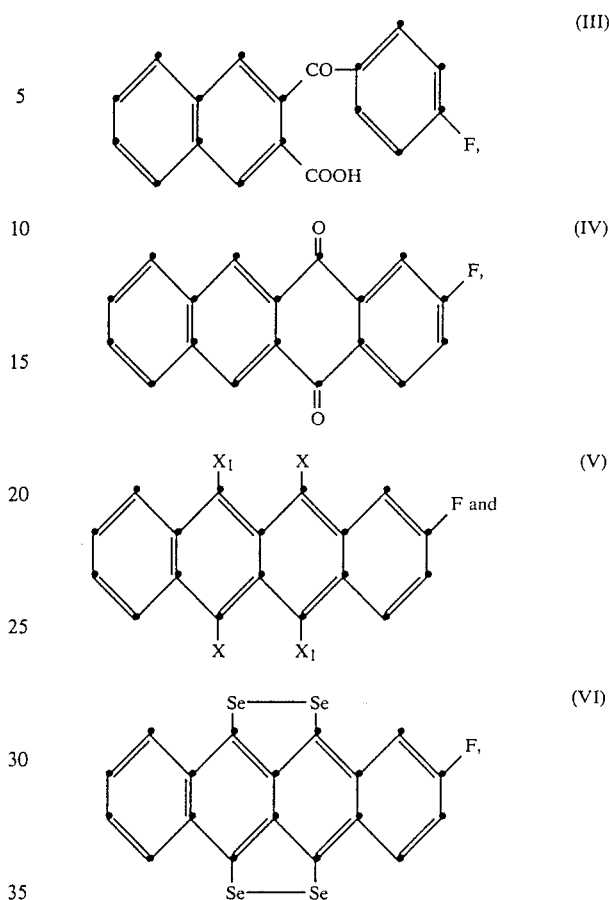

wherein the symbols $X_1$ and X are each hydrogen, or each $X_1$ is hydrogen and each X is chlorine, or each $X_1$ is chlorine and each X is hydrogen.

The compounds of the formulae III to VI can be produced, using processes analogous to known processes, by reacting 2,3-naphthalenecarboxylic anhydride, in the presence of a Friedel-Crafts catalyst, preferably aluminium chloride, with fluorobenzene to give a compound of the formula III; cyclising the 2-(4-fluorobenzoyl)-naphthalene-3-carboxylic acid to 2-fluoro-5,12-naphthacenequinone (compound of the formula IV); reducing the compound of the formula IV to 2-fluorotetracene (compound of the formula V wherein $X_1$ and X=H), for example in the presence of zinc dust in an acid medium, for example acetic acid; reacting the 2-fluorotetracene with sulfuryl chloride to 2-fluoro-5,11- or 2-fluoro-6,12-dichlorotetracene [cp. for example Bull. Soc. Chim. France, 427 (1948)]; and finally reacting the 2-fluoro-5,11- or 2-fluoro-6,12-dichlorotetracene, or mixtures thereof, at elevated temperature with selenium.

The cyclisation of 2-(4-fluorobenzoyl)-naphthalene-3-carboxylic acid to 2-fluoro-5,12-naphthacenequinone can be performed, in a manner known per se, in the presence of a protonic acid or a Lewis acid. Examples of suitable protonic acids are polyphosphoric acid, chlorosulfonic acid and sulfuric acid. Suitable Lewis acids are for example boron trifluoride and particularly aluminium trichloride. Cyclisation in the presence of a Lewis acid, especially aluminium chloride, in the melt is preferred. The reaction of 2-fluorotetracene with sulfuryl chloride and also the reaction of 2-fluoro-5,11- or 2-fluoro-6,12-dichlorotetracene with selenium are advantageously performed in the presence of an inert organic solvent. Suitable for the reaction of 2-fluorotetracene with sulfuryl chloride are for example nitrobenzene, benzene and carbon tetrachloride. The preferred solvent is nitrobenzene. The reaction of 2-fluoro-5,11- or 2-fluoro-6,12-dichlorotetracene is preferably performed in the presence of a halogenated aromatic hydrocarbon, especially trichlorobenzene.

By virtue of the metallically electrical conductivity and the strongly marked electrical and optical anistropy, the complex according to the invention is suitable for use as an organic conductor element, for example for conducting coatings on plastics fibres; also as polariser material, or as an additive to antistatic coatings and coverings, for example those based on plastics material. The complex of the formula I can also be used in highly-conductive, electron-beam- or photon-sensitive printing materials or processes, such as are described for example in the European patent application No. 23 988 and in the U.S. Pat. No. 4,036,648. And by virtue of its redox properties and the various intense colours of its redox stages (blue-green, green, blue, yellow), the complex of the formula I can also be used advantageously in information systems, such as colour picture screens, as well as in electronic components. The highly conductive complex of the formula I is particularly suitable for such purposes since it can be exposed to further oxidation and reduction in electrical arrangements, such as in electrochromic circuits. Because however of its metallic phase stable down to 5° K., the complex according to the invention is suitable in particular for various applications in low-temperature technology, for example for use in condenser films or in active battery electrodes, the use of which is then possible also at low temperature.

EXAMPLE (a) 45.0 g (227 mmols) of 2,3-naphthalenedicarboxylic anhydride are suspended in 200 ml (2.1 mols) of fluorobenzene, and in the course of 5 minutes, with vigorous stirring, 75.5 g (565 mmols) of powdered aluminium chloride are added (exothermic reaction up to about 32° C.). The dark-red suspension is refluxed and stirred for 6 hours, and the solution is then allowed to cool to room temperature; it is subsequently poured onto about 500 g of ice, and is stirred until completion of hydrolysis. Excess fluorobenzene is evaporated off, and the product obtained is suspended in water. The suspension is filtered off, the filtrate is afterwards washed and the product is dried. There are obtained 76 g of crude 2-(4-fluorobenzoyl)-naphthalene-3-carboxylic acid. The crude product is stirred up with 2 liters of 10% sodium carbonate solution; the resulting solution is then acidified with hydrochloric acid, and the white precipitate is filtered off and dried. The yield is 54.2 g (81% of theory) of 2-(4-fluorobenzoyl)-naphthalene-3-carboxylic acid. MS: ($M^+ = 294$; $M^+$—COOH=249, $M^+$—COO=250, $M^+$—$C_6H_4F$=199); IR spectrum (KBr): OH about 3300 $cm^{-1}$; C=O double bands 1695/1705 $cm^{-1}$.

(b) 200 g (1.5 mols) of powdered aluminium chloride and 40 g (684 mmols) of sodium chloride are heated together to 140°–150° C. After about 1½ hours, 40 g (136 mmols) of 2-(4-fluorobenzoyl)-naphthalene-3-carboxylic acid are added to the melt. The dark-red mixture is stirred at 140°–150° C. for one hour; and hydrolysis is subsequently performed at about 100° C. by the slow addition of ice-water. The precipitate is filtered off and then stirred up with 10% sodium carbonate solution. The mixture is afterwards washed neutral with water and dried. The product obtained is sublimed at 230° C. to thus obtain 13.1 g (70% of theory) of 2-fluoro-5,12-naphthacenequinone.

Thin-layer chromatography: silica gel, benzene: $R_x \approx 0.6$; yellow fluorescent spot;
NMR (100 MHz in $CDCl_3$): complicated but interpretable multiplets in the aromatic range;
MS: $M^+ = 276$, $M^+$—CO=248, $M^+$—2CO=220.

(c) 8.0 g (29 mmols) of 2-fluoro-5,12-naphthacenequinone, 40 ml of water, 680 ml of acetic acid and 40 g (611 mmols) of zinc dust are placed together and refluxed. After 30 minutes' stirring under reflux, the mixture is cooled, 200 ml of water are added, and the formed suspension of 2-fluorotetracene is decanted, the zinc dust remaining in the flask. The 2-fluorotetracene is filtered off, washed with water and ethanol and dried. Recrystallisation from 500 ml of xylene yields 4.0 g (56% of theory) of 2-fluorotetracene.

UV spectrum (benzene): typical tetracene spectrum: $\lambda_{max}$ 476, 446, 420, 394 nm;
MS: $M^+ = 246$, $M^{+2} = 123$.

(d) 5.0 g (20.3 mmols) of 2-fluorotetracene are suspended under nitrogen in 25 ml of nitrobenzene, and the suspension is cooled to 5° C. There are then added dropwise, within 30 minutes, 5.9 g (43.7 mmols) of sulfuryl chloride in 25 ml of nitrobenzene, and the mixture is stirred at 5° C. for 2 hours. The temperature is then allowed to rise to 20°–25° C.; the mixture is heated in the course of 1½ hours to 90° C.; it is stirred at this temperature for 10 minutes and afterwards cooled. The suspension is filtered off, and subsequently washed with about 600 ml of ethanol and dried. The yield is 5.0 g (78% of theory) of 2-fluoro-5,11- or 6,12-dichlorotetracene.

MS: $M^+ = 314/316$ (=2 Cl), $M^+$—HCl=278, $M^+$—2Cl=244, $M^{+2} = 157/158$ (2 Cl).

(e) 7.2 g (22.8 mmols) of 2-fluoro-5,11-dichlorotetracene, 7.7 g (97.5 mmols) of selenium and 175 ml of trichlorobenzene are placed together, and are refluxed under nitrogen for 120 hours at a bath temperature of 250° C. A further 3.8 g (48.1 mmols) of selenium are added after 70 hours. The suspension is then allowed to cool; it is subsequently diluted with about 200 ml of n-hexane and filtered off. The product is afterwards washed with benzene and n-hexane, dried, and then sublimed under high vacuum at 260°–270° C./$10^{-3}$ bar. The yield is 4.4 g (35% of theory) of 2-fluoro-5,6,11,12-tetraselenotetracene.

UV spectrum in trichlorobenzene $\lambda_{max} = 719$, 659, 466 nm.

MS (sublimed at 260° C./$10^{-3}$ bar): $M^+ = 560$ (cluster 4 Se), $M^+$—Se=480 (cluster 3 Se), $M^+$—2Se =400 (cluster 2 Se), $M^+$—3Se=322/320, $M^{+2} = 279$ (cluster 4 Se), $M^+$—$C_{18}H_7F$=242; crystal structure: space group $P2_12_12_1$; axes a=21.538 Å, b=17.351 Å, c=4.033 Å.

(f) 30 mg of (2-fluoro-5,6,11,12-tetraselenotetracene)$_2$ are introduced into the anode compartment of an electrolytic cell having a volume of 40 ml, and as electrolyte are added 200 mg of tetra-n-butyl-ammonium bromide. The cell is evacuated overnight in a drying chamber at $5 \times 10^{-2}$ mbar, and then flushed with argon. There are subsequently added, as solvent, 33 ml of a mixture of 90 vol. % of tetrahydrofuran and 10 vol. % of N,N-dimethylformamide. After 12 hours' heating at 60° C., a voltage of 0.6 volt is applied to the cell, whereupon an electrolytic current of 1 μA commences to flow. After 21 days, the crystals formed on the anode (diameter 1 mm; 80% by weight of Pt, 20% by weight of Ir) are detached by washing with ethanol. Six crystals having mean dimensions of 6 mm×50μ×50μ are mounted by means of platinum paste (Pt paste 308 A, Degussa) onto 4 probes consisting of 25μ thick gold wires. The conductivity of the crystals at room temperature, measured in the above probe arrangement, varies from 1000 to 2000 ohm$^{-1}$cm$^{-1}$. The dependence of the specific resistance on temperature, standardised to 295° K., exhibits for all crystals, within an accuracy of measurement of 2%, the behaviour shown in FIG. 2.

What is claimed is:

1. A complex of the formula I

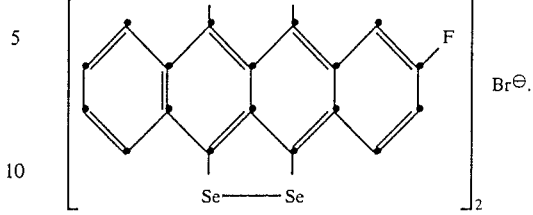

2. Compound of formula

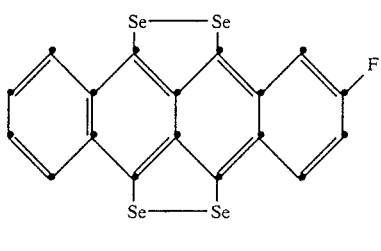

* * * * *